US012667334B2

(12) United States Patent
    Tabata

(10) Patent No.: US 12,667,334 B2
(45) Date of Patent: Jun. 30, 2026

(54) INFORMATION PROCESSING APPARATUS AND ULTRASOUND SYSTEM

(71) Applicant: NIHON KOHDEN CORPORATION, Tokyo (JP)

(72) Inventor: Hiraku Tabata, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 18/695,156

(22) PCT Filed: Oct. 5, 2022

(86) PCT No.: PCT/JP2022/037350
    § 371 (c)(1),
    (2) Date: Mar. 25, 2024

(87) PCT Pub. No.: WO2023/063197
    PCT Pub. Date: Apr. 20, 2023

(65) Prior Publication Data
    US 2024/0389979 A1      Nov. 28, 2024

(30) Foreign Application Priority Data

Oct. 13, 2021    (JP) ................................. 2021-167888

(51) Int. Cl.
    *A61B 8/00*            (2006.01)
(52) U.S. Cl.
    CPC .......... *A61B 8/4455* (2013.01); *A61B 8/4488* (2013.01); *A61B 8/54* (2013.01)
(58) Field of Classification Search
    CPC ....... A61B 8/4455; A61B 8/4488; A61B 8/54; A61B 8/4245; A61B 8/5207; A61B 8/5269; A61B 8/4483
    See application file for complete search history.

(56) References Cited

U.S. PATENT DOCUMENTS

2014/0219061 A1    8/2014  Sakaguchi
2019/0046158 A1*   2/2019  Kroon .................. A61B 8/4236

FOREIGN PATENT DOCUMENTS

EP        3 349 663 A0    3/2017
EP        3 881 770 A1    9/2021
          (Continued)

OTHER PUBLICATIONS

Office Action issued on Nov. 5, 2024 by the Japanese Patent Office in corresponding JP Patent Application No. 2021-167888.
(Continued)

*Primary Examiner* — Kaitlyn E Sebastian
(74) *Attorney, Agent, or Firm* — Sughrue Mion, PLLC

(57)                ABSTRACT

An information processing apparatus configured to process information acquired from a probe including a base having flexibility to bend along a surface of subject's body and a plurality of ultrasound transducers arranged on the base at predetermined intervals. The information processing apparatus includes a controller configured to acquire transmission information, which relates to ultrasound emitted from the ultrasound transducers of the probe whose base is attached to the subject along the surface of the subject's body, and first reception information, which relates to first reflection received by first ultrasound transducers of the ultrasound transducers after the ultrasound is reflected by a first target, and calculate parameters, which relate to a curve of the base, from the transmission information, the first reception information, and the predetermined intervals between the first ultrasound transducers.

13 Claims, 14 Drawing Sheets

(56)        References Cited

FOREIGN PATENT DOCUMENTS

| | | | |
|---|---|---|---|
| JP | 2009-247511 A | 10/2009 | |
| JP | 2010-269060 A | 12/2010 | |
| JP | 2013-75072 A | 4/2013 | |
| JP | 2017-176769 A | 10/2017 | |
| JP | 2018-533385 A | 11/2018 | |
| JP | 2021-49073 A | 4/2021 | |
| WO | WO-2012101511 A2 * | 8/2012 | ........... A61B 8/0883 |
| WO | 2017/046019 A1 | 3/2017 | |

OTHER PUBLICATIONS

International Search Report (PCT/ISA/210) dated Jan. 3, 2023, issued by the International Searching Authority in counterpart International Application No. PCT/JP2022/037350.
Written Opinion (PCT/ISA/237) dated Jan. 3, 2023, issued by the International Searching Authority in counterpart International Application No. PCT/JP2022/037350.

* cited by examiner

121

| INSTRUCTION UNIT | 1211 | INFORMATION ACQUISITION UNIT | 1212 |
| IMAGE GENERATION UNIT | 1213 | CALCULATION UNIT | 1214 |
| COMPENSATION UNIT | 1215 | OUTPUT UNIT | 1216 |

START

S101 — RECEIVE SELECTION OF TRANSDUCERS

S102 — INSTRUCT SELECTED TRANSDUCERS TO EMIT ULTRASOUND

S103 — ACQUIRE TRANSMISSION INFORMATION AND RECEPTION INFORMATION

S104 — GENERATE IMAGE DATA

S105 — CALCULATE PARAMETERS

S106 — COMPENSATE IMAGE DATA

S107 — OUTPUT COMPENSATED IMAGE DATA

END 111 (110)

301     302

110

112

111

114

121

| TRANSDUCER SWITCHING UNIT | 1218 | TRANSDUCER SPECIFICATION UNIT | 1219 |
| INSTRUCTION UNIT | 1211 | INFORMATION ACQUISITION UNIT | 1212 |
| IMAGE GENERATION UNIT | 1213 | CALCULATION UNIT | 1214 |
| COMPENSATION UNIT | 1215 | OUTPUT UNIT | 1216 |

INFORMATION PROCESSING APPARATUS AND ULTRASOUND SYSTEM

CROSS-REFERENCE TO RELATED APPLICATIONS

This application is a National Phase Entry of PCT International Application No. PCT/JP2022/037350 filed on Oct. 5, 2022, which claims priority to Japanese Patent Application No. 2021-167888 filed on Oct. 13, 2021, the contents of all of which are incorporated herein by reference in their entirety.

TECHNICAL FIELD

The present disclosure relates to an information processing apparatus configured to process information acquired from a probe and an ultrasound system including the information processing apparatus.

BACKGROUND

Using ultrasound systems, condition of a blood vessel or blood flow volume through a blood vessel can be checked. In recent years, development of probes for ultrasound systems that are attachable to a surface of subject's body has been promoted. A probe disclosed in Patent Literature 1, for example, includes a flexible base attachable to the surface of subject's body and a plurality of ultrasound transducers arranged in a matrix on the base.

CITATION LIST

Patent Literature

Patent Literature 1: JP2010-269060A

SUMMARY

Technical Problem

It is preferable that ultrasound systems process information acquired from probes according to a shape of a surface of subject's body to which the probes are attached in order to reduce influence of the shape on the information for a highly accurate diagnosis.

The present disclosure provides an information processing apparatus and an ultrasound system in which information acquired from a probe whose base is attached to a subject along a surface of the subject's body is processed according to a shape of the surface of the subject's body.

Solution to Problem

An information processing apparatus of the present disclosure is configured to process information acquired from a probe including a base having flexibility to bend along a surface of subject's body and a plurality of ultrasound transducers arranged on the base at predetermined intervals. The information processing apparatus includes an information acquisition unit and a calculation unit. The information acquisition unit is configured to acquire transmission information, which relates to ultrasound emitted from the ultrasound transducers of the probe whose base is attached to the subject along the surface of the subject's body, and first reception information, which relates to first reflection received by first ultrasound transducers of the ultrasound transducers after the ultrasound is reflected by a first target. The calculation unit is configured to calculate parameters, which relate to a curve of the base, from the transmission information, the first reception information, and the predetermined intervals between the first ultrasound transducers.

Effects of Invention

In the information processing apparatus, the parameters, which relates to the curve of the base along the surface of the subject's body are calculated. Therefore, using the information processing apparatus, it becomes possible to process the information acquired from the probe according to the curve.

BRIEF DESCRIPTION OF DRAWINGS

Exemplary embodiments of the present disclosure will be described in detail based on the following figures.

FIG. 6B is a cross-sectional view taken along a line B-B shown in FIG. 6A.

Figure 7:
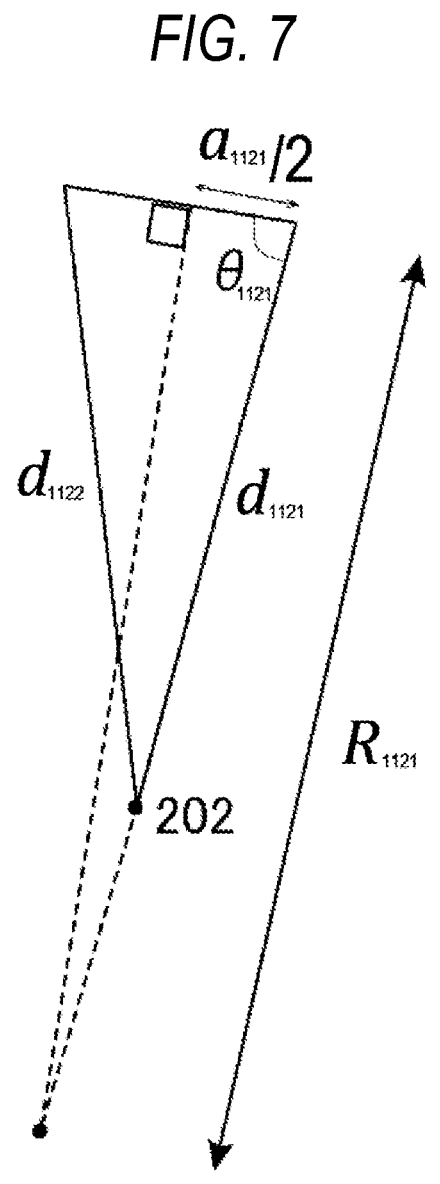

FIG. 7 illustrates an example of how a parameter is calculated by a calculation unit shown in FIG. 5.

DESCRIPTION OF EMBODIMENTS

Figure 1:
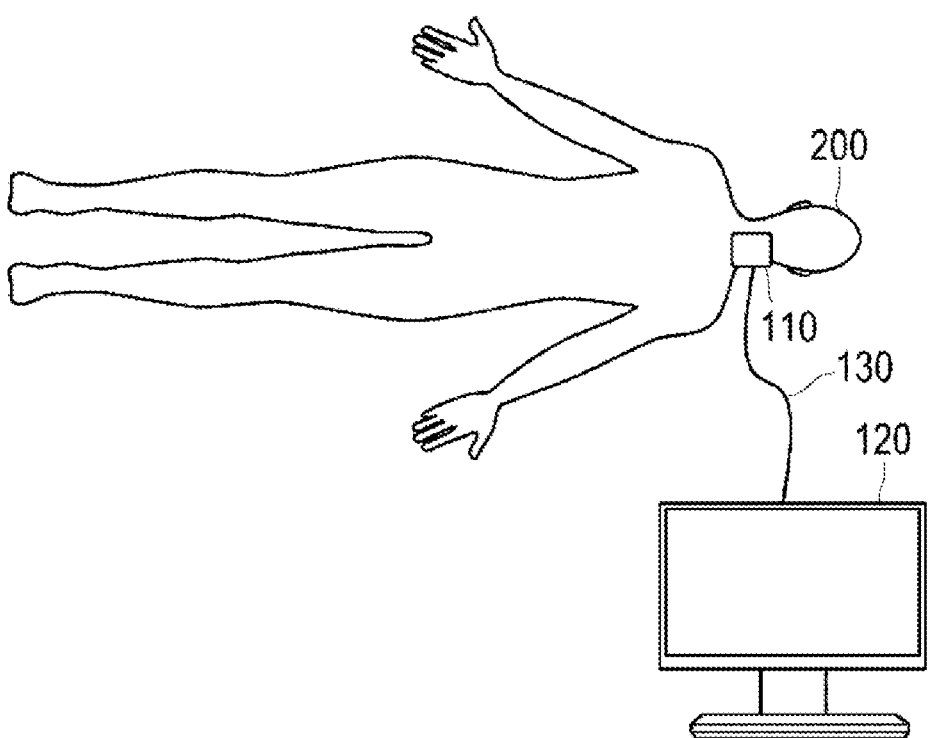
FIG. 1 is a schematic diagram illustrating an exemplary configuration of an ultrasound system according to an embodiment.

In the following, an ultrasound system according to an embodiment of the present disclosure will be described in detail with reference to the drawings. Dimensional ratios in the drawings may be different from actual ratios for the sake of convenience.

Configuration of Ultrasound System

FIG. 1 is a schematic diagram illustrating an exemplary configuration of an ultrasound system 100 according to the present embodiment. The ultrasound system 100 includes, for example, a probe 110, an information processing apparatus 120, and a cable 130. The cable 130 is configured to convey electrical signals between the probe 110 and the information processing apparatus 120. The cable 130 may be provided integrally with or detachable from the probe 110. The cable 130 may include a connector and may be connected to the information processing apparatus 120 by inserting the connector into the information processing apparatus 120. The probe 110 is attachable to a surface of a body of a subject 200. Information that has been acquired from the probe 110 from the subject 200 is transmitted to the information processing apparatus 120 through the cable 130. The information processing apparatus 120 may be, for example, a patient monitoring system or a defibrillator configured to acquire vital sign data, such as blood pressure, oxygen saturation, and respiratory rate, or a computer, such as a server and a personal computer.

Figure 2:
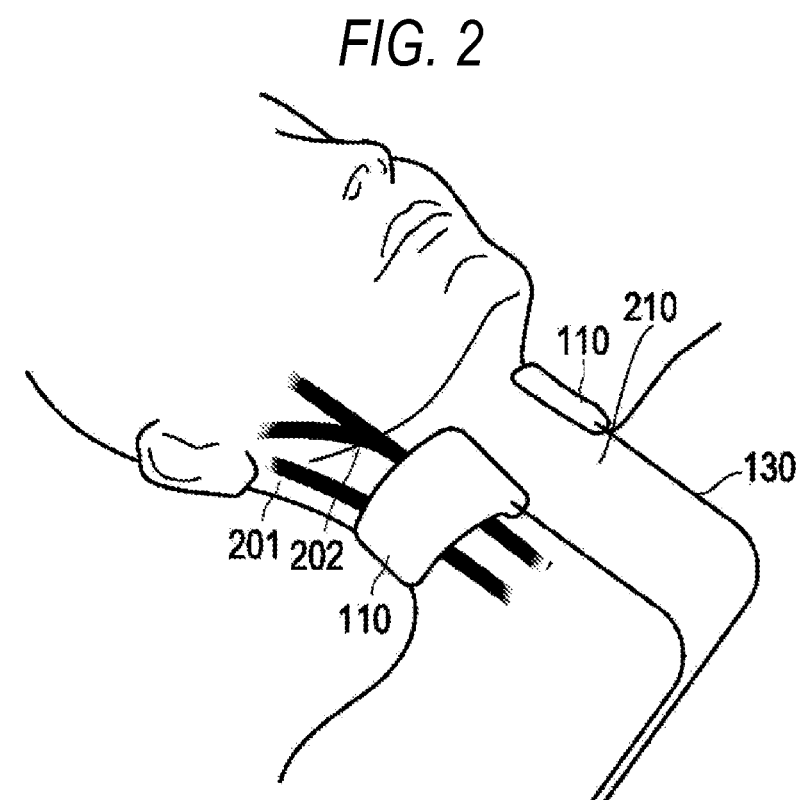
FIG. 2 illustrates an example of how a probe shown in FIG. 1 is attached to a subject.

FIG. 2 illustrates an example of how the probe 110 is attached to the subject 200. The probe 110 is attachable to, for example, the surface of the body of the subject 200. If the probe 100 is attached to the neck 210 of the subject 200, information related to a vertebral artery 201 and a carotid artery 202 of the subject 200 can be acquired from the probe 110. The carotid artery 202 is an example of a target.

Figure 3A:
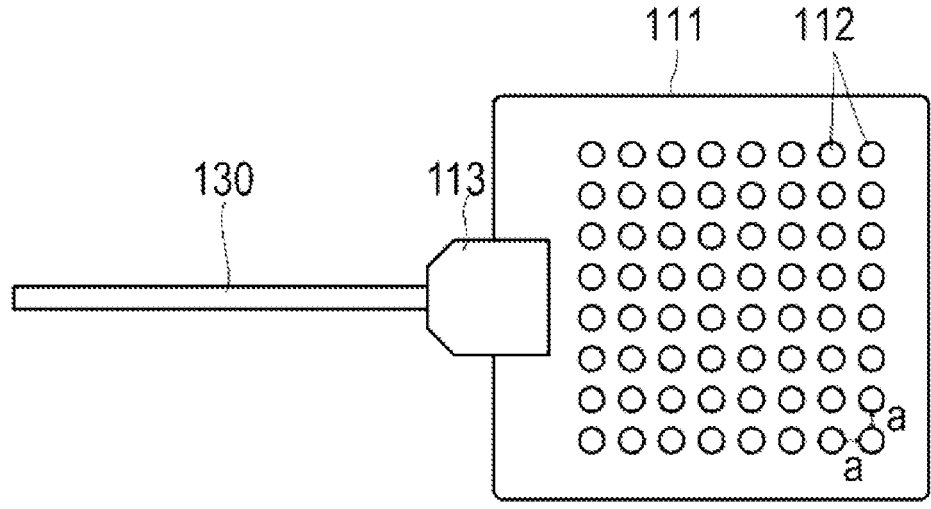
FIG. 3A is a top view of the probe shown in FIG. 1.
Figure 3B:
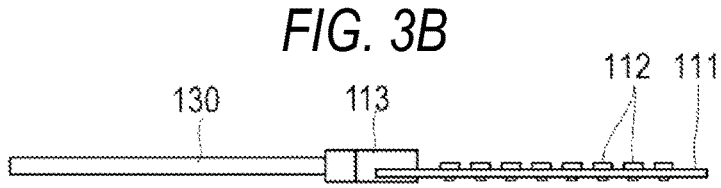
FIG. 3B is a side view of the probe shown in FIG. 1.
Figure 3C:
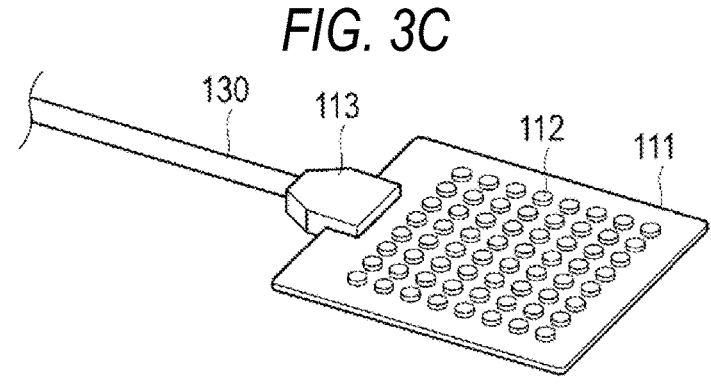
FIG. 3C is a perspective view of the probe shown in FIG. 1.

FIG. 3A is a top view, FIG. 3B is a side view, and FIG. 3C is a perspective view of the probe 110. The probe 110 includes, for example, a base 111, a plurality of ultrasound transducers 112, and a connector 113.

The base 111 has flexibility to bend along the surface to which the base 111 is attached. The base 111 is, for example, a sheetlike member having a quadrangular shape as shown in FIG. 3A. The base 111 is made of resin, such as polyimide resin and silicone.

The ultrasound transducers 112 are, for example, embedded in or mounted on the base 111. Although 64 transducers 112 arranged in an 8×8 matrix are shown in FIGS. 3A to 3C, the number and the arrangement of the transducers 112 are not limited thereto. For example, 96 transducers may be arranged in a 3×32 matrix.

The transducers 112 may be arranged at regular intervals, and the intervals in the row direction may be equal to those in the column direction. The transducers 112 shown in FIG. 3A are arranged at regular intervals a in the row and the column directions. The intervals are not limited thereto as long as they are predetermined. The intervals in the row direction may be different from those in the column direction, and the intervals may vary according to the position in the base 111.

Each of the transducers 112 includes, for example, a piezoelectric element and electrodes. The transducers 112 transmit ultrasound in response to transmission instructions sent from the information processing apparatus 120 via the cable 130. When the transducers 112 receive the ultrasound (hereinafter, referred to as "reflection") that has been reflected by blood vessels, bones, organs, or other tissues in the body of the subject 200, signals are sent from the transducers 112 to the information processing apparatus 120 via the cable 130.

A connector 113 electrically connects the transducers 112 to the cable 130 and may be, for example, a wiring board.

Figure 4:
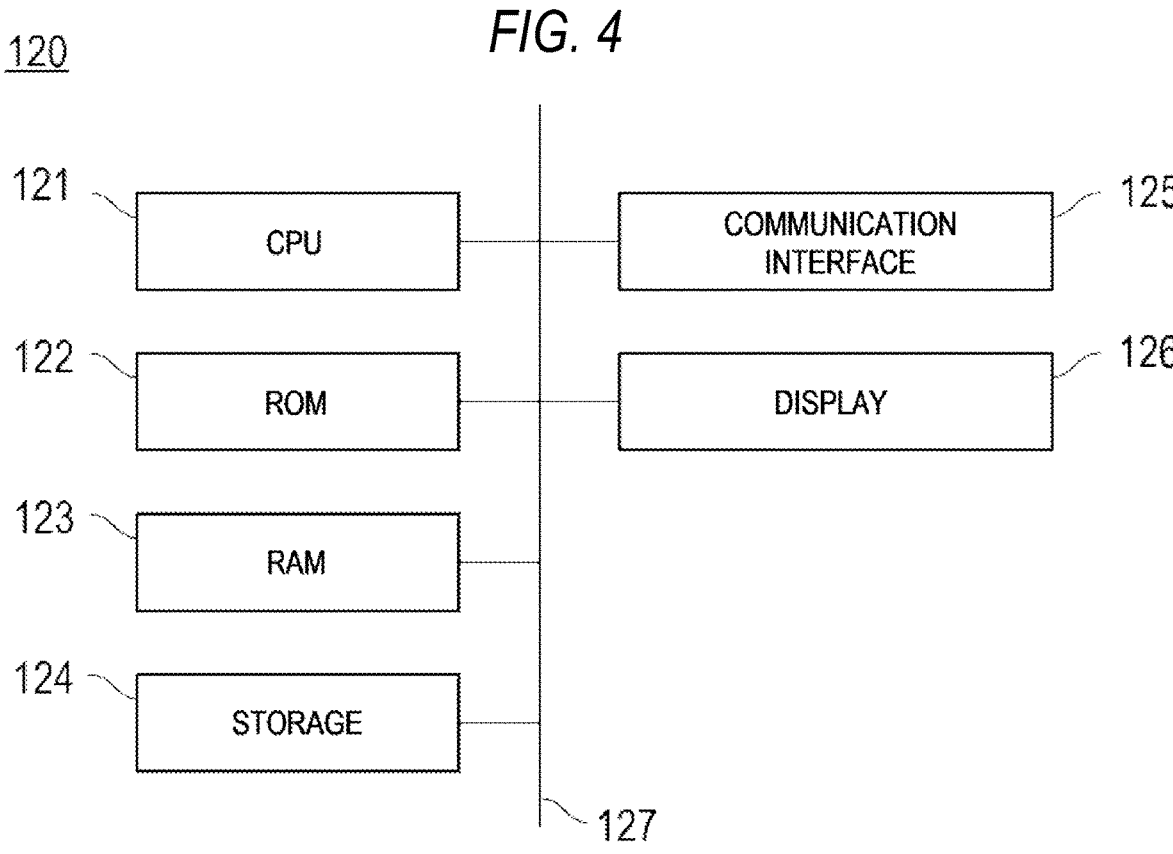
FIG. 4 is an exemplary block diagram of an information processing apparatus shown in FIG. 1.

FIG. 4 is an exemplary block diagram of the information processing apparatus 120. The information processing apparatus 120 includes: a central processing unit (CPU) 121, or processing circuitry; a read-only memory (ROM) 122; a random-access memory (RAM) 123; a storage 124; a communication interface 125; and a display 126. They can communicate with each other through a bus 127.

The CPU 121 is configured to control them and to perform a variety of arithmetic processing according to programs stored in the ROM 122 or the storage 124. The ROM 122 is configured to store programs and data. The RAM 123 is configured to store programs and data temporarily as a cache.

The storage 124 is configured to store programs including an operating system and data. For example, a program for exchanging a variety of information with the probe 110 and a program for analyzing information acquired from the probe 110 are stored in the storage 124. If a machine learning model is used for analyzing the information acquired from the probe 110, a trained model or data for training a model may be stored in the storage 124.

The communication interface 125 is a wired or wireless interface for communicating with external devices. The cable 130 may be connected to the communication interface 125.

The display 126 is, for example, a touch panel configured to receive a variety of input from a user. The display 126 is an example of an input reception unit. Using the display 126, the user can select some of the transducers 112 to cause them to emit ultrasound. The input from the user is transmitted to the CPU 121. The display 126 may be a combination of an input device and a display. In this case, the input device may be, for example, buttons, a mouse, or a keyboard.

Figures 5, 6A:
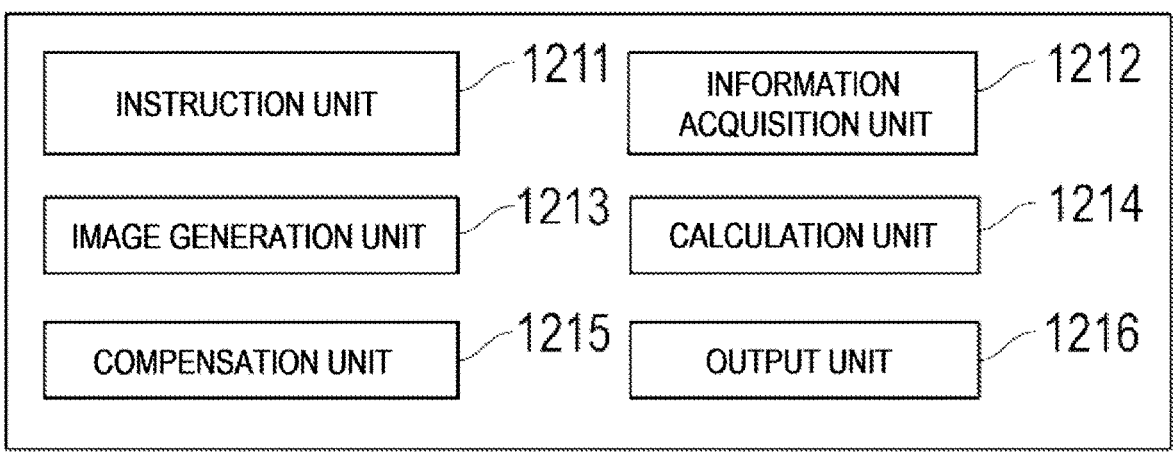
FIG. 5 illustrates an exemplary functional configuration of a CPU shown in FIG. 4.
FIG. 6A is a perspective view of the probe attached to a neck of the subject.

FIG. 5 illustrates an exemplary functional configuration of the CPU 121. The CPU 121 is configured to perform functionality of an instruction unit 1211, an information acquisition unit 1212, an image generation unit 1213, a calculation unit 1214, a compensation unit 1215, and an output unit 1216 by performing processing according to a program loaded from the storage 124.

The instruction unit 1211 is configured to give some of the transducers 112 selected by the user instructions, through the cable 130, to emit ultrasound.

The acquisition unit 1212 is configured to acquire transmission information and reception information. The transmission information is information relating to ultrasound that has been emitted from some of the transducers 112 and includes, for example, a position, a drive voltage, a drive frequency, and a gain of the transducers 112, a waveform of the ultrasound, and a starting time and duration of the emission. The reception information is information relating to reflection that was reflected by, for example, the carotid artery 202 and has been received by some of the transducers 112 and includes, for example, a frequency, a waveform, and an intensity of the reflection, and a time of the reception. When ultrasound has been transmitted from one of the transducers 112, its reflection may be received by some or all of the transducers 112.

The information acquisition unit 1212 is configured to acquire the transmission information from the instruction unit 1211 and to acquire the reception information from the transducers 112 via the communication interface 125. The transmission information may be acquired from the transducers 112 that have emitted ultrasound. The information acquisition unit 1212 may further acquire information related to reflection that was reflected by blood vessels (for example, the vertebral artery 201) other than the carotid artery 202, bones, organs, or other tissues and has been received by the transducers 112. That is, the information acquisition unit 1212 may acquire information related to reflection that was reflected by a plurality of targets and has been received by the transducers 112. In this case, it becomes possible to calculate parameters to be described later with high accuracy.

The image generation unit 1213 is configured to generate image data of the vertebral artery 201, the carotid artery 202, and the like of the subject 200 based on the information acquired from the probe 110. The transmission information and the reception information may be used for the generation of the image data. The image generation unit 1213 generates, for example, M-mode, B-mode, color Doppler mode, or pulsed wave Doppler mode images by processing the information acquired from the probe 110.

The calculation unit 1214 is configured to calculate the parameters, which relate to the curve of the base 111 along the surface of the body of the subject 200 for reducing a warp of an image due to the curve.

The parameters are calculated from the transmission information, the reception information, and the intervals between the transducers 112 that has received reflection. The calculation unit 1214 calculates, for example, angles $\theta 1121$, $\theta 1122$, and $\theta 1123$ shown in FIG. 6B as the parameters.

Figure 6B:
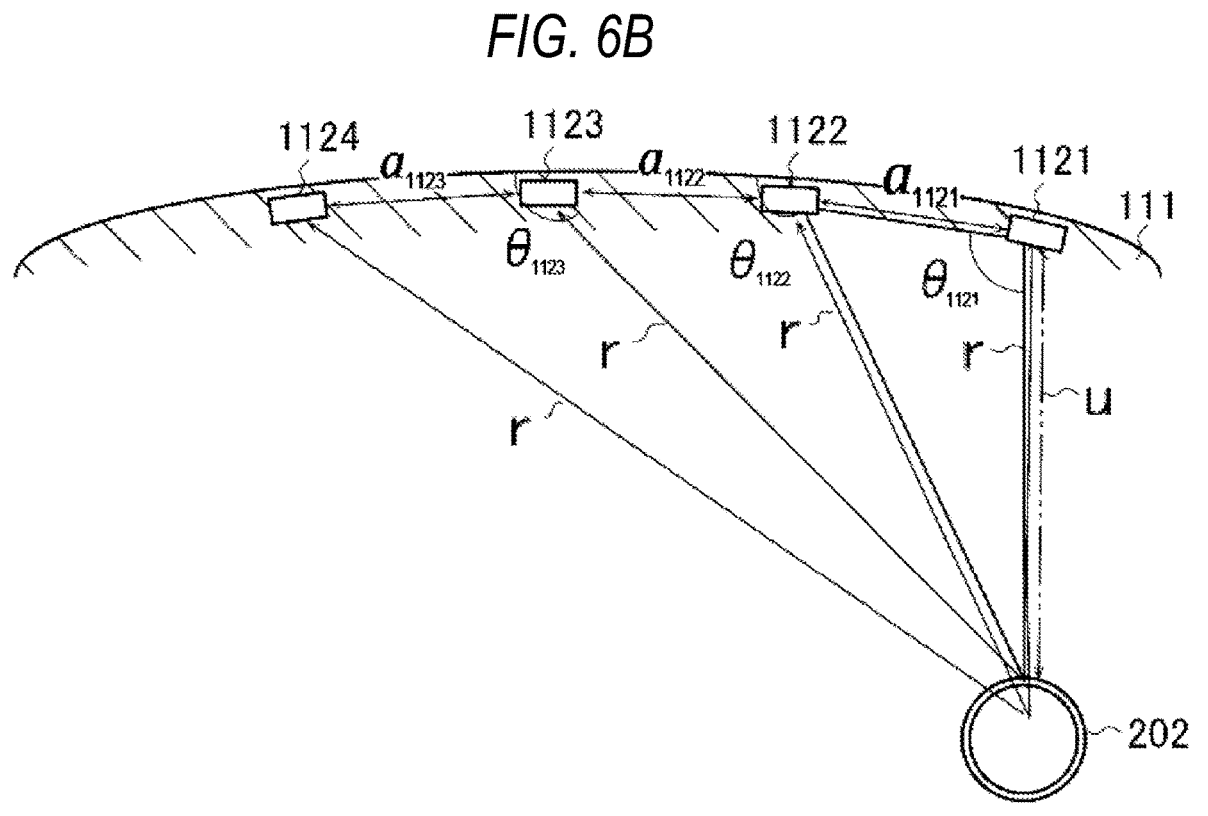

An example of how the angles are calculated by the calculation unit 1214 will be described with reference to FIGS. 6A and 6B. FIG. 6A is a perspective view of the probe 110 attached to the neck 210, and FIG. 6B is a cross-sectional view taken along a line B-B shown in FIG. 6A. Although the target in the following example is the carotid artery 202, the target may be another blood vessel (for example, the vertebral artery 201). If ultrasound u is emitted from a transducer 1121 of the transducers 112 and is then reflected by a wall of the carotid artery 202, reflection r of the ultrasound u will be received by four adjacent transducers 1121, 1122, 1123, and 1124 of the transducers 112.

In this case, the calculation unit 1214 first calculates a propagation delay, which is a timelag between the emission of the ultrasound u from the ultrasound transducer 1121 and the reception of the reflection r by each of the transducers 1121, 1122, 1123, and 1124. The propagation delay is calculable from the transmission information and the reception information. In the following, t1121 denotes the propagation delay of the transducer 1121, t1122 of the transducer 1122, t1123 of the transducer 1123, and t1124 of the transducer 1124.

Next, the calculation unit 1214 calculate a distance between the wall of the carotid artery 202 and each of the transducers 1121 to 1124 from the propagation delays t1121 to t1124 and the velocity v of the ultrasound u in the body of the subject 200. The distance di between the wall of the carotid artery 202 and the transducer i is calculable from Math. 1. The velocity v is, for example, 1540 m/s.

$$d_i = v\left(t_i - \frac{1}{2}t_{1121}\right) \qquad \text{[Math. 1]}$$

Next, the calculation unit 1214 calculates the angles from the distances d1121 to d1124. Specifically, the calculation unit 1214 calculates: the angle $\theta 1121$ between a straight line connecting the carotid artery 202 and the transducer 1121 and a straight line connecting the adjacent transducers 1121 and 1122; the angle $\theta 1122$ between a straight line connecting the carotid artery 202 and the transducer 1122 and a straight line connecting the adjacent transducers 1122 and 1123; and the angle $\theta 1123$ between a straight line connecting the carotid artery 202 and the transducer 1123 and a straight line connecting the adjacent transducer 1123 and 1124. Given that the transducers 1121 to 1124 are arranged at the predetermined intervals as shown in FIG. 6B, the calculation unit 1214 finally calculates the angles $\theta 1121$ to $\theta 1123$ from Math. 2, which is derived from the law of cosines.

$$\cos \theta_i = \frac{a_i^2 + d_i^2 - d_{i+1}^2}{2a_i d_i} \qquad \text{[Math. 2]}$$

It is preferable that the number of the transducers 112 that have received the reflection r be not less than three when the calculation unit 1214 calculates the angles. The calculation unit 1214 may calculate angles between straight lines connecting the vertebral artery 201 (or another artery) and each of the transducers 112.

The calculation unit 1214 may calculate radii of curvature of the curve as the parameters.

The radius of curvature R1121 of the curve formed by the adjacent transducers 1121 and 1122, which is shown in FIG. 6B, the radius of curvature R1122 of the curve formed by the adjacent transducers 1122 and 1123, and the radius of curvature R1123 of the curve formed by the adjacent transducers 1123 and 1124 are calculable from Math. 3.

$$\frac{1}{2}a_i = R_i \cos \theta_i \qquad \text{[Math. 3]}$$

The compensation unit 1215 is configured to compensate the image data generated by the image generation unit 1213 based on the parameters.

Figure 8A:
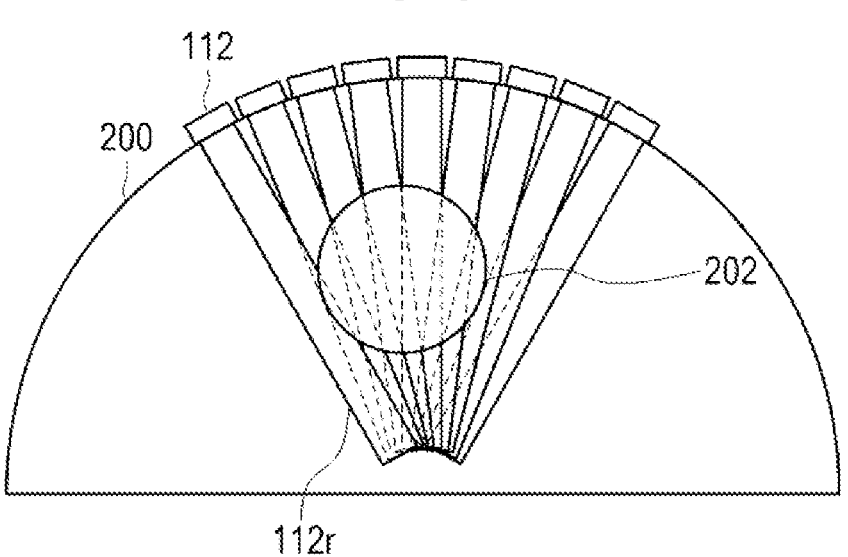
FIG. 8A is a schematic view illustrating uncompensated imaging regions assigned to ultrasound transducers.
Figure 8B:
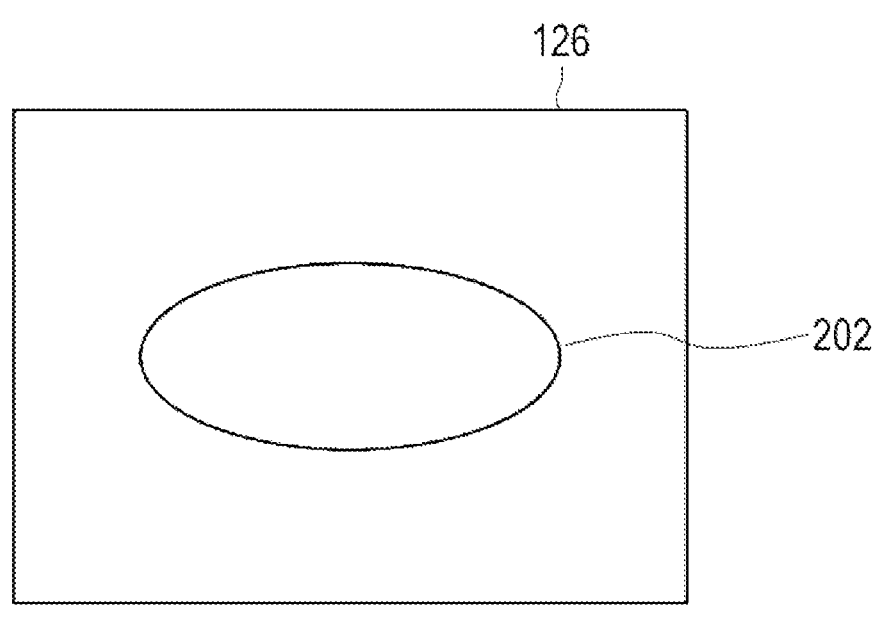
FIG. 8B is a schematic view illustrating an image of a carotid artery generated based on the imaging regions shown in FIG. 8A.

FIG. 8A is a schematic view illustrating uncompensated imaging regions 112r assigned to the transducers 112, and FIG. 8B is a schematic view illustrating an image of the carotid artery 202 generated based on the uncompensated imaging regions 112r. In this case, since imaging processing is performed regardless of the curve, the imaging regions 112r having overlaps shown by dotted lines in FIG. 8A are stretched as if the base 111 were attached to a flat surface. Therefore, if the base 111 is attached to a curved surface, the generated image of the carotid artery 202 is warped as shown in FIG. 8B.

Figures 9A, 9B:
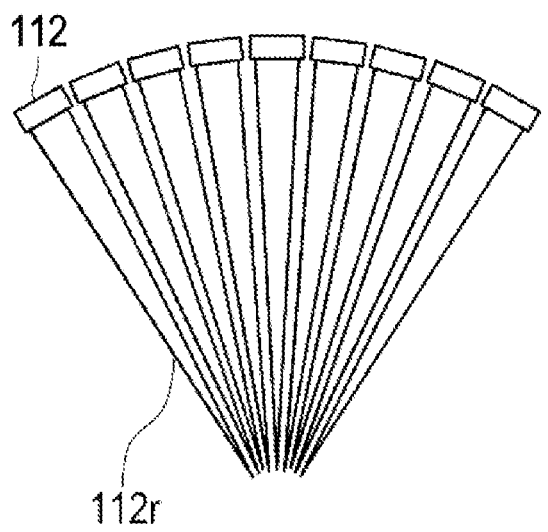
FIG. 9A is a schematic view illustrating compensated imaging regions assigned to the ultrasound transducers.
FIG. 9B is a schematic view illustrating an image of the carotid artery generated based on the imaging regions shown in FIG. 9A.

FIG. 9A is a schematic view illustrating the imaging regions 112r compensated by the compensation unit 1215, and FIG. 9B is a schematic view illustrating an image of the carotid artery 202 generated based on the compensated imaging regions 112r. Based on the parameters calculated by the calculation unit 1214, it can be postulated that each of the imaging regions 112r has, for example, a fan shape or an isosceles triangular shape approximately. In this case, the overlaps shown by the dotted lines in FIG. 8A are eliminated, and the generated image reflects more exact shape of the carotid artery 202.

The compensation unit 1215 may compensate, based on the parameters, a cross-sectional area of the carotid artery 202 that is calculable from its image data.

The output unit 1216 is configured to output the compensated image data, for example, to the display 126. The output unit 1216 may further output the compensated cross-sectional area of the carotid artery 202. The output unit 1216 may further output information related to blood flow volume through the carotid artery 202 that is calculable from its color Doppler or pulsed wave Doppler mode images or is calculable from its cross-sectional area and the blood flow velocity.

Figure 10:
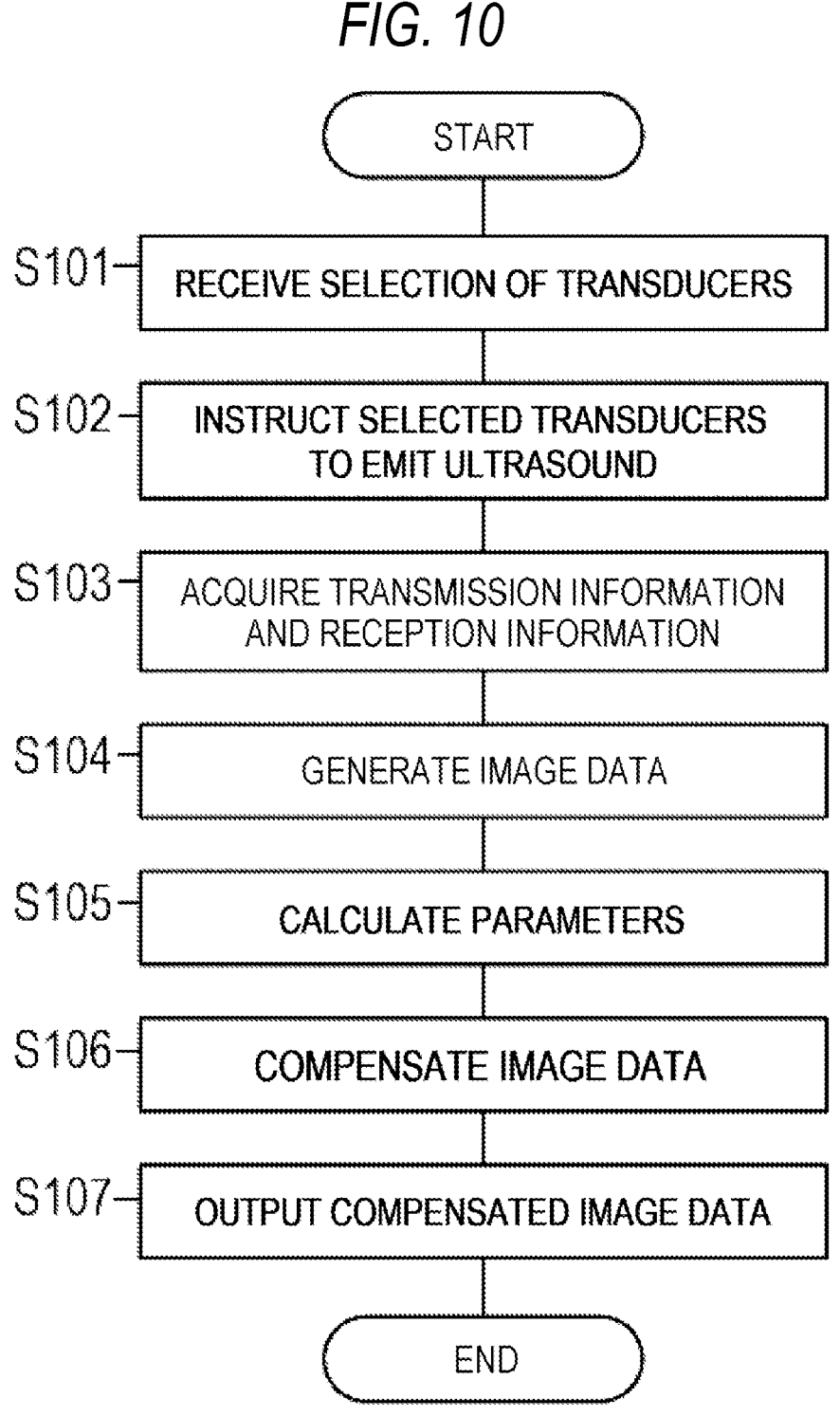
FIG. 10 is an exemplary flowchart illustrating processing performed by the information processing apparatus shown in FIG. 1.

Processing Performed by Information Processing Apparatus FIG. 10 is an exemplary flowchart illustrating processing performed by the information processing apparatus 120. The information processing apparatus 120 is configured to acquire information from, for example, the probe 110 attached to the neck 210 of the subject 200.

First, the information processing apparatus 120 receives the input of the selection of the transducers 112 to be caused to emit ultrasound (step S101). For example, the user inputs the selection using the display 126, and then the information processing apparatus 120 receives the selection. The user may view an uncompensated image of the carotid artery 202 displayed on the display while selecting, for example, the transducers 112 that are close to the carotid artery 202.

Next, the information processing apparatus 120 instructs the selected transducers 112 to emit ultrasound (step S102). The instructions are sent, for example, via the communication interface 125.

Next, the information processing apparatus 120 acquires the transmission information and the reception information (step S103) and then generates the image data of the carotid artery 202 based on the information acquired from the probe 110 (step S104).

Next, the information processing apparatus 120 calculates the parameters (step S105).

Next, the information processing apparatus 120 compensates the image data generated in step S104 based on the parameters calculated in step S105 (step S106). Finally, the information processing apparatus 120 outputs the image data compensated in step S106 (step S107) and ends the processing.

Advantageous Effects of Information Processing Apparatus and Ultrasound System

In the information processing apparatus 120 and the ultrasound system 100 of the present embodiment, the image data generated based on the reception information are compensated according to the parameters. Therefore, it becomes possible to reduce the influence of the shape on the image data output from the ultrasound system 100 for a highly accurate diagnosis.

As for rigid probes, since they do not bend when attached to the surface of subject's body, the shape of the surface to which they are attached have little or no influence on the output information. It is difficult, however, to attach such probes to the subject 200.

On the other hand, since the probe 110 includes the base 111, which has flexibility to bend along the surface of the subject 200, the user can easily attach the probe 110 to the surface of the subject 200.

The probe 110 has a problem, however, that the information acquired from the probe 110 may be affected by the curve. The information processing apparatus 120 calculates the parameters, which relates to the curve, and compensates the image data based on the parameters to reduce the influence of the shape on the information. Therefore, the ultrasound system 100 can output exact image data of the vertebral artery 201, the carotid artery 202, and the like.

Figure 11:
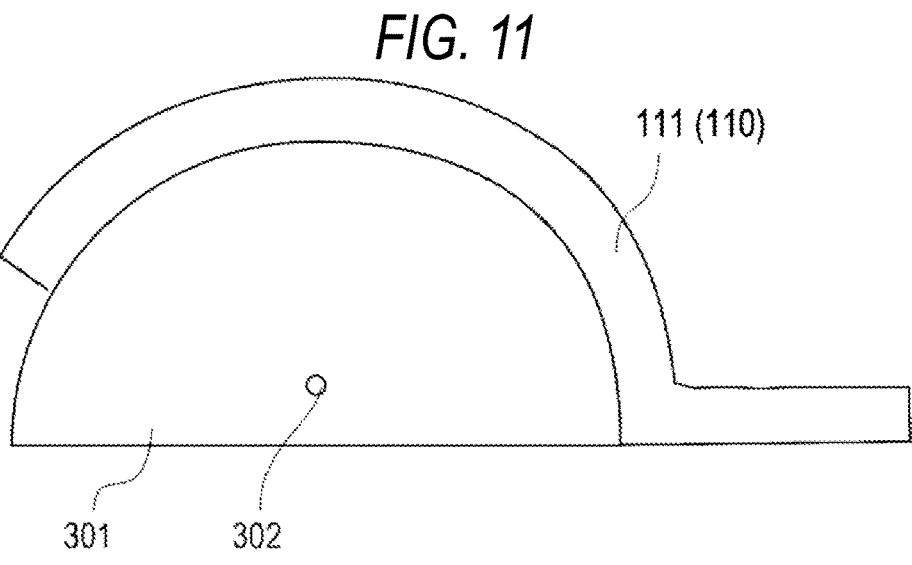
FIG. 11 illustrates an experimental system for demonstrating effectiveness of compensation.

FIG. 11 illustrates an experimental system for demonstrating effectiveness of the compensation. Imaging phantom 301 and an ultrasound reflector 302 embedded in the imaging phantom 301 were used in the experiment. The ultrasound reflector 302 was made of a metal. The imaging phantom 301 was mainly made of agar and had a curved surface having a uniform curvature. The probe 110 was attached to the imaging phantom 301 along its curved surface. One of the transducers 112 was caused to emit ultrasound.

Figure 12A:
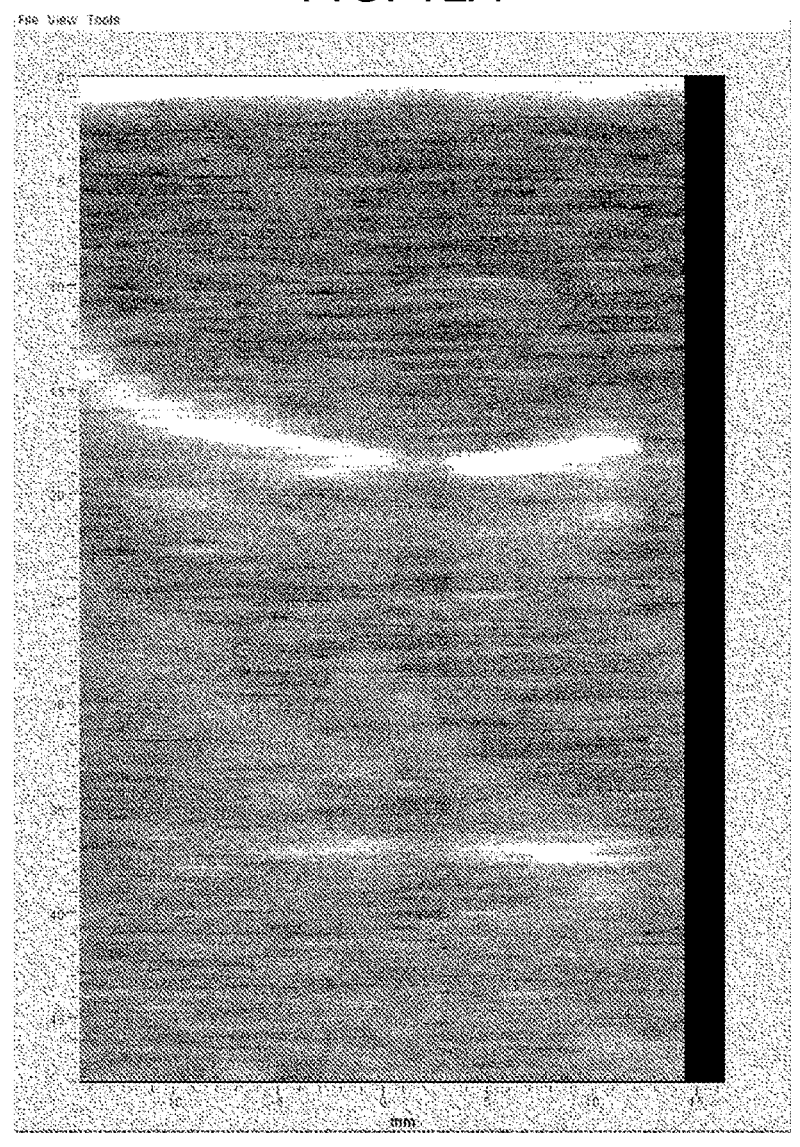
FIG. 12A is an uncompensated image obtained in an experiment using imaging phantom.
Figure 12B:
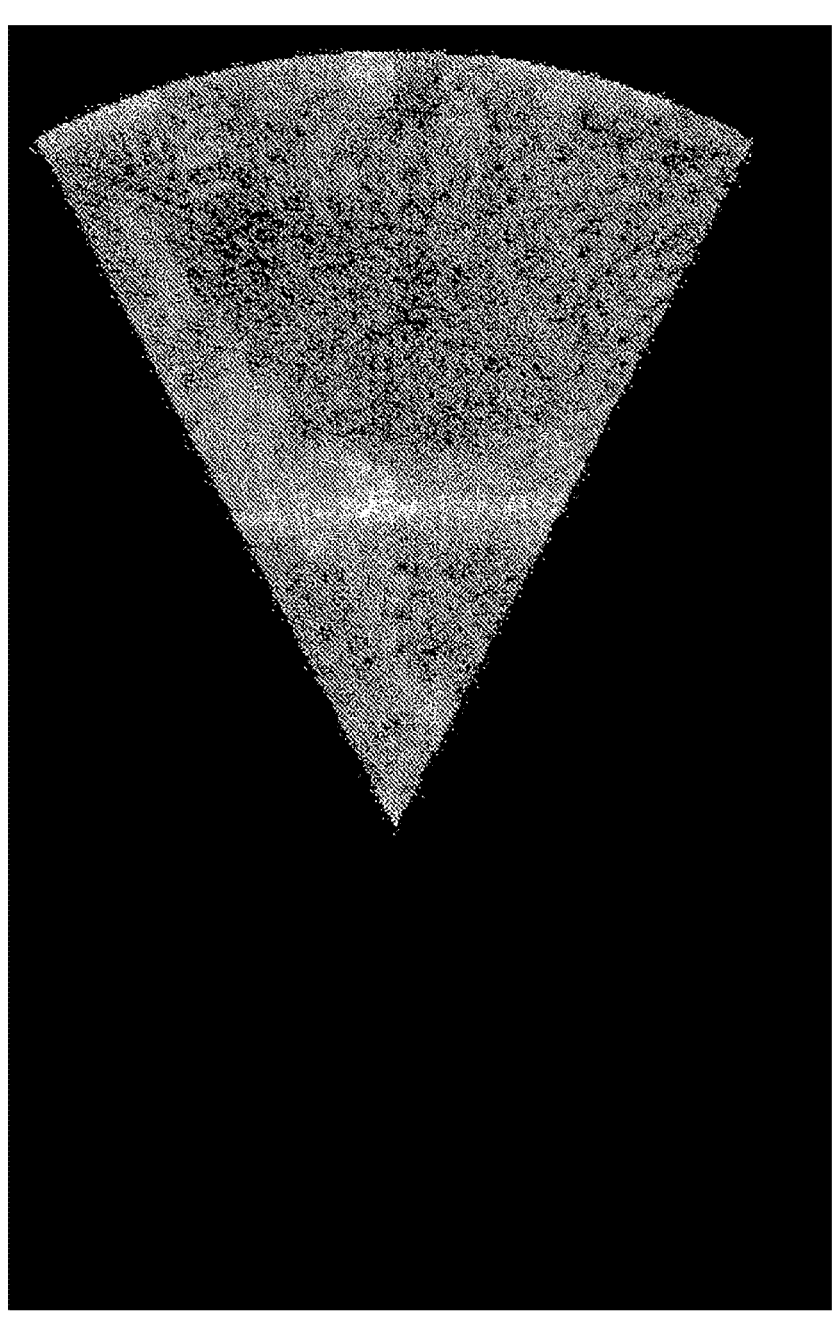
FIG. 12B is a compensated image obtained in the experiment.
Figure 13:
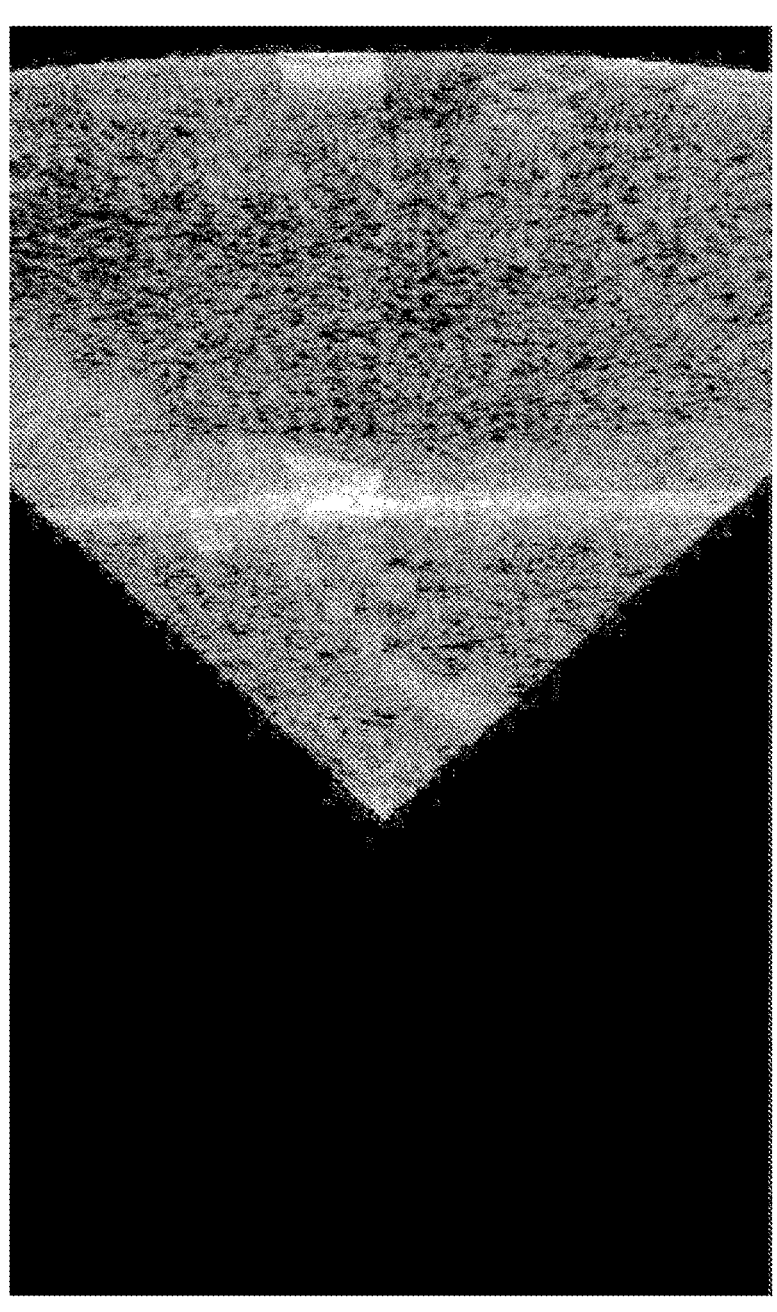
FIG. 13 is an enlarged view of FIG. 12B.

FIGS. 12A, 12B, and 13 are B-mode images obtained in the experiment. FIG. 12A is an uncompensated image, and FIG. 12B an compensated image. FIG. 13 is an enlarged view of FIG. 12B.

In the uncompensated B-mode image of FIG. 12A, the surface corresponding to the bottom of the imaging phantom 301 is curved due to the curve of the base 111. On the other hand, in the compensated B-mode image of FIGS. 12B and 13, that surface is straighter than that in the FIG. 12A. Therefore, it can be concluded that the compensation reduces the influence of the shape on the B-mode image.

It should be added that the parameters may also be used for other purposes, such as compensation of the blood flow velocity through the carotid artery 202. In addition, the compensated image data may be used only for internal processing and do not have to be displayed.

As described above, in the information processing apparatus 120 and the ultrasound system 100 of the present embodiment, the information acquired from the probe 110 is processed according to the parameters. Therefore, it becomes possible to reduce the influence of the curve on the information output from the ultrasound system 100 for a highly accurate diagnosis.

Since the ultrasound system 100 enables doctors, nurses, or other persons to attach the probe 110 to a patient in a short time and to monitor blood flow volume or the like for a long time in a hands-free manner, the ultrasound system 100 is suitable for emergency medical care. For example, by monitoring the blood flow volume through the carotid artery 202, the quality of chest compressions can be continuously checked.

Figure 14:
FIG. 14 is a cross-sectional view of a probe according to a first modification.

In the following, some modifications of the ultrasound system 100 will be described. Descriptions of similar configurations will be omitted for the sake of simplicity.
First Modification FIG. 14 is a cross-sectional view of a probe 110 according to a first modification. The probe 110 according to the first modification further includes an ultrasound reflector 114, which is embedded in the base 111.

The reflector 114 has acoustic impedance different from acoustic impedance of the base 111 and is provided at a predetermined position in the base 111. The information processing apparatus 120 acquires ultrasound that was emitted from the transducers 112 and has been reflected by the reflector 114. The information processing apparatus 120 calculates the parameters from the transmission information and the reception information. The reflector 114 is an example of the target.

The reflector 114 has, for example, a needlelike shape and extends substantially parallel to the base 111. Although the reflector 114 can be made of any material as long as it has acoustic impedance different from that of the base 111, it may be made of, for example, metal. The reflector 114 may be hollow inside. A plurality of reflector 114 may be provided in the base 111.

Similarly to the embodiment described above, using the ultrasound system 100 including the probe 110 according to the first modification, it is possible to calculate the parameters to process the reception information acquired from the probe 110 based on the parameters. Further, by storing information relating to a position of the reflector 114 in advance in the information processing apparatus 120, the information processing apparatus 120 can easily identify which transducers 112 are close to the reflector 114 and can cause some or all of them to emit ultrasound. In this case, since a time required to identify which transducers 112 are to be caused to emit ultrasound or to identify which transducers emitted ultrasound that has passed through the reflector 114 can be shortened, it becomes possible to calculate the parameters quickly.

Second Modification

Figure 15:
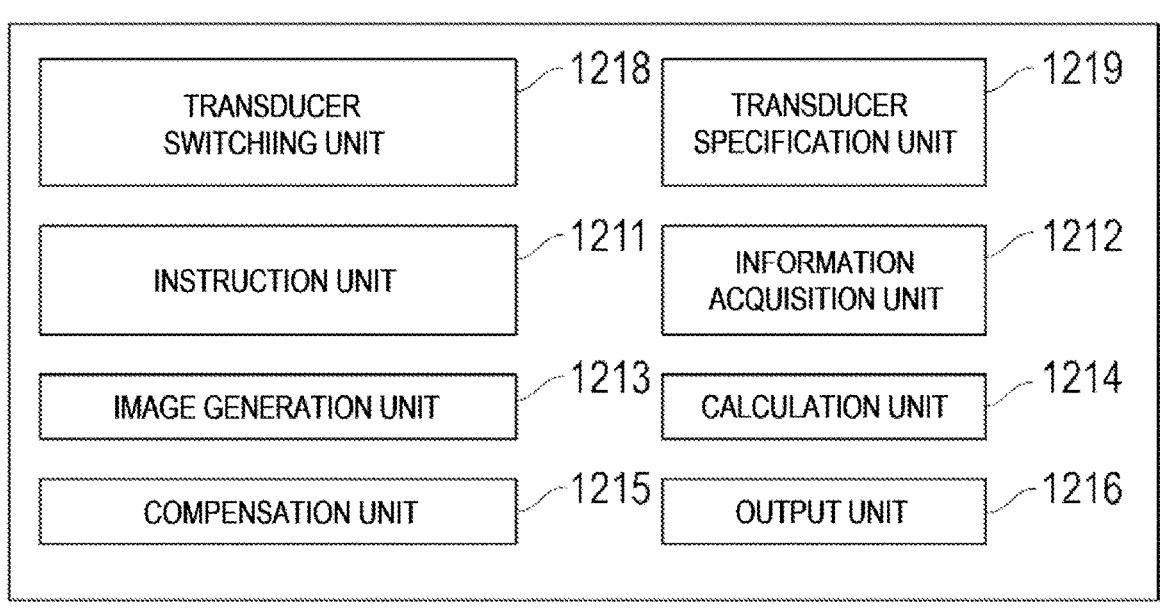
FIG. 15 illustrates an exemplary functional configuration of a CPU according to a second modification.

FIG. 15 illustrates an exemplary functional configuration of a CPU 121 according to a second modification. The CPU 121 according to the second modification is configured to perform functionality of a transducer switching unit 1218 and a transducer specification unit 1219 in addition to the instruction unit 1211, the information acquisition unit 1212, the image generation unit 1213, the calculation unit 1214, the compensation unit 1215, and the output unit 1216.

The transducer switching unit 1218 is configured to successively switch the transducers 112 that are caused to emit ultrasound, for example, in a scanning manner in the row or the column direction of the matrix.

The transducer specification unit 1219 is configured to identify which transducers 112 are close to, for example, the carotid artery 202. The transducer identification unit 1219 may identify such transducers 112 based on whether reflection that has been received by each of the transducers 112 follows a predetermined pattern or not (for example, a peculiar pattern of amplitude). For example, if one of the transducers 112 receives reflection following a pattern peculiar to that reflected by the carotid artery 202, the transducer specification unit 1219 determines that that transducer 112 is close to the carotid artery 202. If one of the transducers 112 receives the reflection that does not follow the pattern, the transducer specification unit 1219 determines that that transducer 112 is apart from the carotid artery 202. The transducer specification unit 1219 may identify which transducers 112 are close to the reflector 114, which is shown in FIG. 14.

The instruction unit 1211 according to the second modification is configured to cause some or all of the transducers 112 that are determined to be close to the carotid artery 202 by the specification unit 1219 to emit ultrasound.

Figure 16:
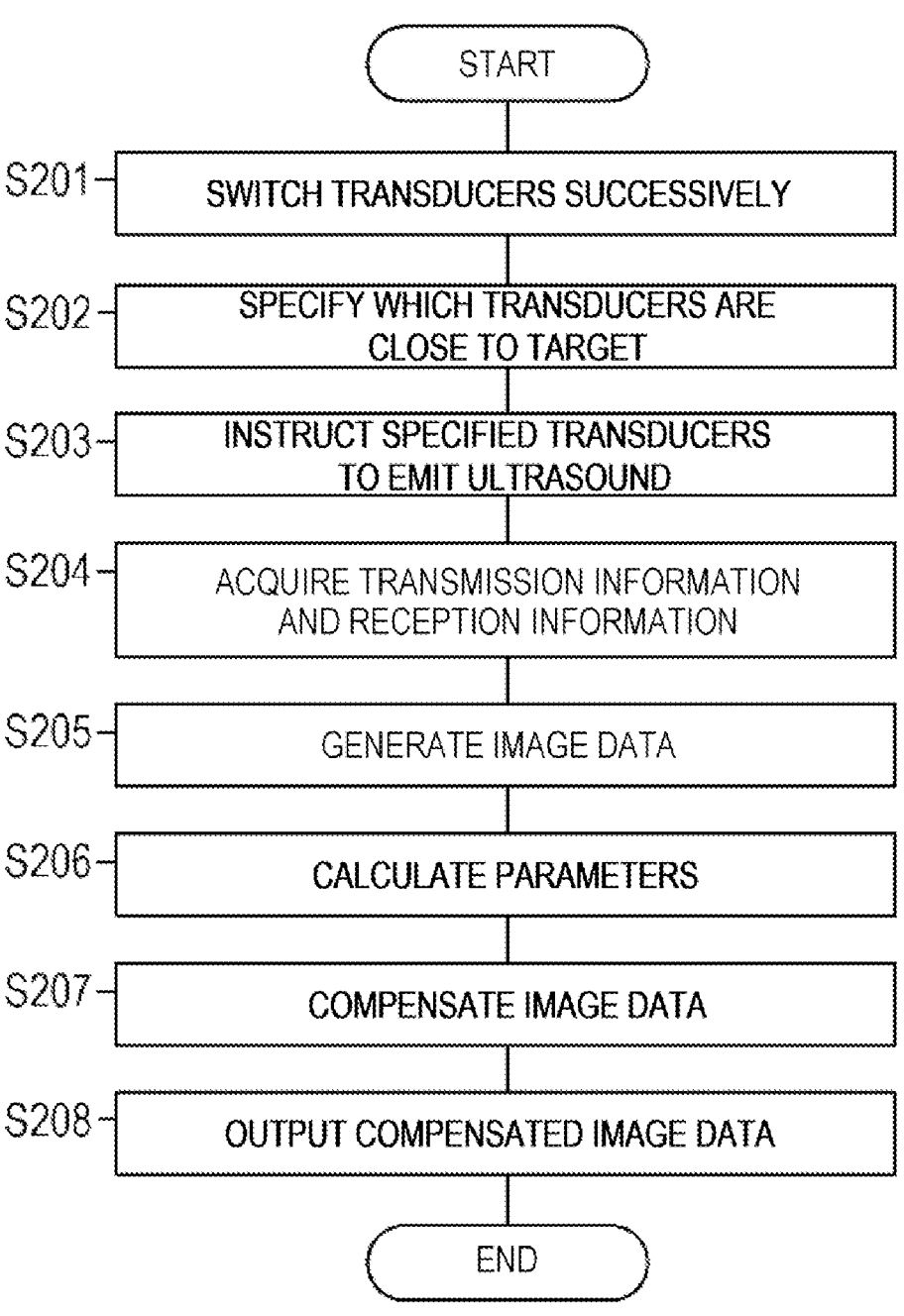
FIG. 16 is an exemplary flowchart illustrating processing performed by the information processing apparatus shown in FIG. 15.

FIG. 16 is an exemplary flowchart illustrating processing performed by the information processing apparatus 120 including the CPU 121 according to the second modification.

First, the information processing apparatus 120 successively switches the transducers 112 that are caused to emit ultrasound (step S201). Next, the information processing apparatus 120 identifies which transducers 112 are close to, for example, the carotid artery 202 based on whether reflection that has been received by each of the transducers 112, which are successively switched in step S201, follows the predetermined pattern or not (step S202). Next, the information processing apparatus 120 instructs some or all of the transducers 112 that are identified in step S202 to emit ultrasound (step S203).

Next, the information processing apparatus 120 acquires the transmission information and the reception information (step S204) and generates the image data of the carotid artery 202 based on the reception information (step S205).

Next, the information processing apparatus 120 calculates the parameters (step S206) and compensates the image data generated in step S205 based on the parameters calculated in step S206 (step S207). Finally, the information processing apparatus 120 outputs the image data compensated in step S207 (step S208) and ends the processing.

Similarly to the embodiment described above, using the ultrasound system 100 including the CPU 121 according to the second modification, it is possible to calculate the parameters to process the reception information based on the parameters. Further, since it is identified which transducers 112 are close to, for example, the carotid artery 202, it becomes possible to diagnose the subject 200 or to monitor their vital signs more accurately.

Although some embodiments of the information processing apparatus of the present disclosure have been described, it goes without saying that addition, modification, or omission can be made as appropriate by those skilled in the art within the scope of the technical scope of the present disclosure.

For example, the target is not only the carotid artery 202 but also may be blood vessels, bones, organs, or other tissues that are anatomically noteworthy.

The probe 110 may be attached not only to the neck 210 of the subject 200 but also to other portions of the subject 200. In addition, the probe 110 does not have to be fixed on the subject 200 continuously but may be pressed against the subject 200 intermittently.

The information processing apparatus 120 does not have to output image data and may output, for example, information related to a cross-sectional area of a blood vessel or blood flow volume through a blood vessel calculated based on the parameters.

The information processing apparatus 120 may generate compensated image data not only by compensating uncompensated image data based on the parameters but also by directly generating image data based on the parameters.

The parameters are not only angles or radii of curvature but also may be other parameters.

The functionality of the information processing apparatus 120 may be implemented using circuitry or processing circuitry that includes general-purpose processors, special-purpose processors, integrated circuits, application-specific integrated circuits, conventional circuitry, and/or combinations thereof that are configured or programmed to perform the disclosed functionality. Processors are considered circuitry or processing circuitry as they include transistors and other circuitry therein. In the present disclosure, the circuitry or units are hardware that carry out or are programmed to perform the recited functionality. The hardware may be any hardware disclosed herein or otherwise known that is programmed or configured to carry out the recited functionality. When the hardware is a processor that may be considered a type of circuitry, the circuitry or units are a combination of hardware and software, the software being used to configure the hardware and/or processor. The software may be provided using, for example, a non-transitory computer-readable medium, such as a compact disc read-only memory, or a network, such as the Internet. In this case, the software may be transferred to and stored in a memory or a hard disk drive. The software may be preloaded or to be installed timely.

Division of steps in the flowcharts is merely an example. Each step may be divided into more steps, and some steps may be united.

The invention claimed is:

1. An information processing apparatus configured to process information acquired from a probe including a base having flexibility to bend along a surface of a subject's body and ultrasound transducers arranged on the base at predetermined intervals, the information processing apparatus comprising:

a controller configured to:

acquire:

transmission information, which relates to ultrasound emitted from the ultrasound transducers of the probe whose base is attached to the subject along the surface of the subject's body; and first reception information, which relates to first reflection received by first ultrasound transducers of the ultrasound transducers after the ultrasound is reflected by a first target; and calculate parameters, which relate to a curve of the base, from the transmission information, the first reception information, and the predetermined intervals between the first ultrasound transducers, wherein the controller is further configured to:

identify which ultrasound transducers are close to the first target; and cause only some of the ultrasound transducers determined to be close to the first target by the controller to emit the ultrasound, the controller is further configured to:

successively switch the ultrasound transducers to emit the ultrasound; and identify which ultrasound transducers are close to the first target based on whether reflection that has been received by each of the ultrasound transducers follows a predetermined pattern corresponding to the first target.

2. The information processing apparatus according to claim 1, wherein the controller is configured to calculate the parameters from distances between the first target and each of the first ultrasound transducers and the predetermined intervals between the first ultrasound transducers.

3. The information processing apparatus according to claim 1, wherein the parameters include angles between straight lines connecting the first target and each of the first ultrasound transducers.

4. The information processing apparatus according to claim 1, wherein the parameters include radii of curvature of the curve.

5. The information processing apparatus according to claim 1, wherein the controller is further configured to:

generate an image data based on the first reception information;

compensate the image data based on the parameters; and output the compensated image data.

6. The information processing apparatus according to claim 1, further comprising:

an input reception unit configured to receive selection of the ultrasound transducers to be caused to emit the ultrasound, wherein the controller is further configured to cause the selected ultrasound transducers to emit the ultrasound.

7. The information processing apparatus according to claim 1, wherein the controller is configured to acquire the first reception information relating to the first reflection received by the first ultrasound transducers after the ultrasound is reflected by a reflector embedded in the base.

8. The information processing apparatus according to claim 1, wherein the controller is further configured to:

acquire second reception information, which relates to second reflection received by second ultrasound transducers of the ultrasound transducers after the ultrasound is reflected by a second target, and calculate the parameters from the transmission information, the first and the second reception information, the predetermined intervals between the first ultrasound transducers, and the predetermined intervals between the second ultrasound transducers.

9. An ultrasonic processing system, comprising:

a probe including a base having flexibility to bend along a surface of subject's body and ultrasound transducers arranged on the base at predetermined intervals; and the information processing apparatus according to claim 1.

10. The information processing apparatus according to claim 1, wherein the controller is further configured to:

identify which ultrasound transducers are close to the first target based on whether reflection that has been received by each of the ultrasound transducers follows a predetermined pattern of amplitude that is peculiar to reflections from the first target.

11. The information processing apparatus according to claim 10, wherein the first target is a carotid artery.

12. An information processing apparatus configured to process information acquired from a probe including a base having flexibility to bend along a surface of a subject's body and ultrasound transducers arranged on the base at predetermined intervals, the information processing apparatus comprising:

a controller configured to:

acquire:

transmission information, which relates to ultrasound emitted from the ultrasound transducers of the probe whose base is attached to the subject along the surface of the subject's body; and first reception information, which relates to first reflection received by first ultrasound transducers of the ultrasound transducers after the ultrasound is reflected by a first target; and calculate parameters, which relate to a curve of the base, from the transmission information, the first reception information, and the predetermined intervals between the first ultrasound transducers, wherein the controller is further configured to:

acquire the first reception information relating to the first reflection received by the first ultrasound transducers after the ultrasound is reflected by the first target, the first target being embedded in the base.

13. An ultrasonic processing system, comprising:

a probe including a base having flexibility to bend along a surface of subject's body and ultrasound transducers arranged on the base at predetermined intervals; and the information processing apparatus according to claim 12.

* * * * *